United States Patent [19]

Crossley et al.

[11] Patent Number: 4,546,187
[45] Date of Patent: Oct. 8, 1985

[54] PIPERIDINOALKYLTHIO PYRIDINIUM COMPOUNDS

[75] Inventors: Roger Crossley; Kay H. Dickinson, both of Reading, England

[73] Assignee: John Wyeth & Brother Limited, Maidenhead, England

[21] Appl. No.: 507,203

[22] Filed: Jun. 23, 1983

Related U.S. Application Data

[60] Division of Ser. No. 351,837, Feb. 24, 1982, Pat. No. 4,415,582, which is a division of Ser. No. 217,925, Dec. 18, 1980, Pat. No. 4,343,805, which is a continuation-in-part of Ser. No. 98,421, Nov. 29, 1979, abandoned.

[30] Foreign Application Priority Data

Dec. 16, 1978 [GB] United Kingdom ............... 48813/78

[51] Int. Cl.$^4$ .......................................... C07D 401/12
[52] U.S. Cl. .................................................. 546/193
[58] Field of Search ......................................... 546/193

[56] References Cited

FOREIGN PATENT DOCUMENTS 1041342  3/1963  United Kingdom .
1054338  7/1964  United Kingdom .

OTHER PUBLICATIONS

Palmer, The Structure and Reactions of Heterocyclic Compounds, Edward Arnold Ltd., London, 1970, p. 24.

*Primary Examiner*—Jane T. Fan
*Attorney, Agent, or Firm*—George Tarnowski

[57] ABSTRACT

The invention concerns novel compounds of formula I $$X-A-S-Y \qquad (I)$$

wherein X is a radical selected from imidazolyl, pyridyl, quinolyl, tetrahydropyridyl or piperidyl any of which may be substituted and Y is any of the above radicals or a pyridinium radical, A is alkylene of 1–6 carbon atoms. Most of the compounds are anti-ulcer agents but some have anti-hypertensive activity, e.g. where X is quinolyl. Methods of treating ulcers and anti-ulcer compositions are also described.

1 Claim, No Drawings

PIPERIDINOALKYLTHIO PYRIDINIUM COMPOUNDS

This is a division of application Ser. No. 351,837 filed Feb. 24, 1982, now U.S. Pat. No. 4,415,582 issued Nov. 15, 1983, which is a division of application Ser. No. 217,925 filed Dec. 18, 1980, now U.S. Pat. No. 4,343,805 issued Aug. 10, 1982, which is a continuation of application Ser. No. 98,421 filed Nov. 29, 1979, now abandoned.

The invention relates to novel heterocyclic compounds which have anti-ulcer, anti-secretory, and/or anti-hypertensive activity.

During the course of our search for novel anti-ulcer agents we have found that certain novel compounds which have two particular heterocyclic rings (identified below) linked by an alkylene chain containing a sulphur atom, possess anti-ulcer and/or anti-secretory activity. Some of the compounds also have anti-hypertensive activity. Many of the compounds of our invention contain an imidazolyl ring. Some related nitroimidazoles have been disclosed recently in *Arzneimittel Forschung* 1978, 351-366. These compounds have been investigated for activity against various protozoa but so far as we are aware there has been no report of any investigation for anti-ulcer activity. The related compounds of our invention are distinguished from those of this publication by the absence of a nitro group.

German Offenlegungsschrift No. 2,504,252 discloses a wide range of heterocyclic compounds which are said to either inhibit or stimulate gastric secretion. The compounds of our invention are distinguished from those of this German publication by having different combinations of heterocyclic radicals.

According to the present invention, in one aspect, there is provided a compound of the formula I

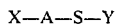

X—A—S—Y    (I)

wherein X is a heterocyclic radical of the formula

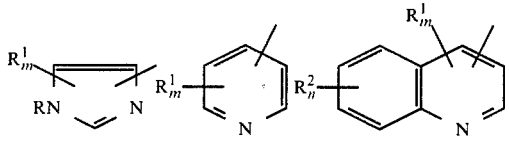

(II)    (III)    (IV)

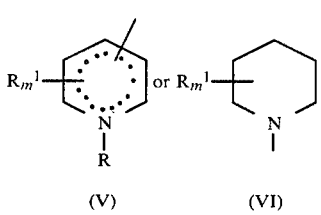

(V)    (VI)

wherein R is hydrogen or lower alkyl, $R^1$ is hydrogen, lower alkyl, hydroxylower alkyl, loweralkoxyloweralkyl, loweralkoxy, halogen, formyl, phenyl, phenylalkyl or acetal [$CH(OR^4)_2$ where $R^4$ is lower alkyl or two $R^4$ radicals are joined to form a lower alkylene chain], $R^2$ is hydrogen, lower alkyl, aryl, arylloweralkyl, halogen, nitro, loweralkoxy, hydroxy, amino, loweralkylamino, diloweralkylamino, trifluoromethyl or two $R^2$ radicals form a loweralkylene dioxygroup, n is 1, 2 or 3, m is 1 or 2, the dotted lines in formula V represent an optional double bond in one of the indicated positions, A is a saturated or unsaturated alkylene radical having from 1 to 6 carbon atoms, which may be substituted by lower alkyl of 1 to 6 carbon atoms; S is sulphur; Y is a heterocyclic radical of formula II to V as defined above, or of formula VII as defined below:

(VII)

wherein $R^1$ and m are as defined above, $R^3$ is loweralkyl, phenyl or aralkyl of 7 to 12 carbon atoms, and $Z^-$ is an anion, and acid addition salts thereof, with the provisos that:

(1) when X and Y are both radicals of formula II at least one substituent R in X or Y is lower alkyl;
(2) when X is a radical of formula II and Y is a radical of formula III and both $R^1$ substituents are hydrogen then R is other than methyl,
(3) when X is a radical of formula III, then Y is a radical of formula III, IV, V or VII,
(4) when X is a 2-quinolyl radical and Y is a radical of formula II, III, IV, or V then the Y radical is linked to S at a position other than the 2-position,
(5) when X is a radical of formula II and Y is a radical of formula VII when A is $CH_2$,
(6) when more than one $R^1$ radical is present in the molecule then the $R^1$ radicals may be the same of different, and
(7) when more than one $R^2$ radical is present in the molecule then the $R^2$ radicals may be the same or different.

Preferably Y is a radical of formula (VII), especially when X is a radical of formula II.

The radical A is preferably a saturated or unsaturated alkylene radical of 1 to 6 carbon atoms which is unsubstituted. A may be methylene, ethylene, propylene, butylene, pentylene, or hexylene. Alternatively A may be unsaturated containing at least one double bond eg —CH=CHCH₂—. A radicals containing 1 to 4 carbon atoms are preferred, especially —CH₂—.

The anion $Z^-$ is preferably halide, namely fluoride, bromide, chloride or iodide or loweralkyl-, aryl- or aralkylsulphonate, eg methyl sulphonate (mesyl) or p-toluene sulphonate (tosyl).

In this specification when a group is substituted by alkyl, this is preferably lower alkyl of 1 to 6 carbon atoms e.g. methyl, ethyl, n-propyl, isopropyl, n-butyl, s-butyl, t-butyl, n-pentyl and n-hexyl. An alkoxy substituent is preferably lower alkoxy in which the alkyl portion is as defined for a lower alkyl group. Whenever the term lower alkyl is used as part of another radical e.g. arylloweralkyl, the lower alkyl portion has 1 to 6 carbon atoms.

The acid addition salts of compounds of formula I may be of an organic or inorganic acid e.g. hydrochloric, hydrobromic, phosphoric, sulphuric, nitric, citric, acetic, formic, fumaric, maleic, tartaric, embonic, methane sulphonic and p-toluene sulphonic acids.

The invention includes a pharmaceutical composition comprising a compound of formula I as defined above where proviso (2) does not apply or an acid addition salt thereof, and a pharmaceutically acceptable carrier.

For the pharmaceutical carrier any suitable carrier known in the art can be used to prepare the pharmaceutical compositions. In such a composition, the carrier may be a solid, liquid, or mixture of a solid and a liquid. Solid form compositions include powders, tablets and capsules. A solid carrier can be one or more substances which may also act as flavouring agents, lubricants, solubilisers suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutitons, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more e.g. 25 mg to 250 mg, according to the particular need and the activity of the active ingredient. The invention also includes the compounds in the absence of carrier where the compounds are in unit dosage form.

The anti-ulcer composititons of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

Anti-ulcer activity was determined by the stress-induced erosion test of Senay & Levine, *Proc. Soc. Exp. Biol. Med.*, 124, 1221-3(1967) and anti-secretory activity by the test of H. Shay, D. Sun and H. Greenstein, *Gastroenterology*, 1954, 26, 903-13 as exemplified by Beattie et al *J. Med. Chem.*, 20, 714 (1977). Compounds which possess one or both these activities are considered to be anti-ulcer agents which can be used for the treatment of ulcers or hypersecretion in mammals. Nearly all compounds of formula I which we have tested possess one or both of the above activities. However, some compounds show activity in tests for anti-hypertensive activity.

In another aspect the invention provides as an anti-ulcer agent a compound of formula I or an acid addition salt thereof as defined above, wherein proviso (2) does not apply, X is other than formula (IV), and if X has formula III then A is at the 2-position of radical III.

The compounds may be prepared by methods known for analogous compounds. The invention includes methods of preparing the novel compounds of the invention. For example a particularly useful method according to the invention comprises reacting a compound of formula VIII

$$X-A-Hal \quad \quad (VIII)$$

where X and A are as defined above and Hal is a halogen atom, with a thiol compound of formula

Y—SH where Y is as defined above and provisos 1–5 apply for an alkali-metal derivative (where possible) of said thiol compound except when Y is VII. The thiol compound may be in the form of a tautomeric thione in suitable cases.

The invention includes a method of preparing novel compounds of formula I wherein Y is a radical of formula VII and $R^3$ is alkyl or aralkyl which method comprises reacting a corresponding compound of formula I wherein Y is a radical of formula III, with an alkylating or aralkylating agent containing the groups $R^3$ and Z, eg with an alkyl or aralkyl halide or a lower alkyl or aralkyl ester of an organic sulphonic acid such as a loweralkyl-, aralkyl- or aryl-sulphonic acid.

A compound I in which $Z^-$ is one particular anion may be converted to another in which $Z^-$ is a different anion by anion exchange, eg chloride may be exchanged for iodide by reaction of a chloride of formula I with sodium iodide in ethanol or other suitable solvent.

The following examples illustrate the invention:

EXAMPLE 1

1-Methyl-2(4-[5-methylimidazolyl]methylthio)-pyridinium chloride

1-Methyl-2-pyridothione (0.63 g, 0.005 mole) in hot ethanol (3 ml) was added to a refluxing solution of 4-chloromethyl-5-methylimidazole, hydrochloride (0.83 g, 0.005 mole) in ethanol (4 ml). The solution was warmed on a steam bath for 5 minutes and allowed to crystallise. The crystals were removed by filtration, washed with ethanol and diethyl ether and dried to give the title compound as the hydrochloride salt (0.75 g) mp>260° C. (Found: C, 44.9; H, 5.35; N, 14.6. $C_{11}H_{14}ClN_3S$, HCl requires C, 45.2; H, 5.2; N, 14.4%).

EXAMPLE 2

1-Methyl-2((2-pyridyl)methylthio)pyridinium chloride 1-methyl-2-pyridothione (1.1 g) was added to a solution of 2-chloromethylpyridine, hydrochloride (1.28 g) in acetonitrile (10 ml). The solution was warmed 10 minutes on a steam bath and allowed to crystallise. The crystals were removed by filtration, washed with ether and dried to give the title compound as the hydrochloride salt (2.0 g) mp 190° C. decomp. (Found: C, 49.4; H, 4.8; N, 9.4. $C_{12}H_{13}N_2SCl.HCl$ requires C, 49.8; H, 4.9; N, 9.7%).

EXAMPLE 3

1-Methyl-2(4-imidazolylmethylthio)pyridinium chloride

4-Chloromethylimidazole, hydrochloride (1.5 g) in ethanol (5 ml) was treated with 1-methyl-2-pyridothione (1.25 g) in ethanol (5 ml) and the mixture was heated on a steam bath for 5 minutes. The solution was allowed to stand for 2 hours, scratched to induce crystallisation and ether (20 ml) was added. The crystals were removed by filtration, washed with ether and dried to give the title compound as the hydrochloride salt (1.5 g) mp 228°–9° C. (Found: C, 43.1; H, 4.7; N, 15.1. $C_{10}H_{12}N_3SCl$, HCl requires C, 43.2; H, 4.7; N, 15.1%).

EXAMPLE 4

1-Methyl-2(4-[5-methylimidazolyl]methylthio)imidazole

A solution of 4-chloromethyl-5-methylimidazole, hydrochloride (1.67 g) in hot ethanol (12 ml) was filtered and treated with a solution of 2-mercapto-1-methylimidazole (1.14 g) in hot ethanol (4 ml). The mixture was heated on a steam bath for 2 hours and then allowed to cool. The resulting solid was removed by filtration and washed with diethyl ether, followed by absolute ethanol and dried to give the title compound as the dihydrochloride monohydrate (1.4 g, 46%) mp 114°–7° C. (Found: C, 36.15; H, 5.5; N, 19.1%. $C_9H_{12}N_4S.2HCl.H_2O$ requires: C, 36.1; H, 5.4; N, 18.7%.

EXAMPLE 5

1-Methyl-2-(3-pyridylmethylthio)pyridinium chloride

A solution of 1-methyl-2-pyridothione (1.25 g) and 3-chloromethylpyridine, hydrochloride (1.66 g) in ethanol (10 ml) was heated under reflux for 5 hours. The product was induced to crystallise by scratching, removed by filtration, washed with ether and dried to give the title compound as the hydrochloride salt (2.2 g) mp 210°–2° C. (Found: C, 44.9; H, 5.2; N, 9.6. $C_{12}H_{13}ClN_2S.HCl$ requires C, 49.8; H, 4.9; N, 9.7%).

EXAMPLE 6

2-(4-[5-Methylimidazolyl]methylthio)pyridine

A solution of 4-chloromethyl-5-methylimidazole, hydrochloride (1.67 g) in hot ethanol (20 ml) was filtered and treated with a solution of 2-mercaptopyridine (1.1 g) in hot ethanol (10 ml). The mixture was refluxed for 3 hours and then cooled to room temperature. Diethyl ether was added and the resulting solid was removed by filtration and dried to give the title compound as the dihydrochloride salt (1.78 g, 64%) mp 203°–6° C. (Found: C, 42.8; H, 4.9; N, 15.45%. $C_{10}H_{11}N_3S.2HCl$ requires: C, 43.2; H, 4.7; N, 15.1%).

EXAMPLE 7

4-(4-[5-Methylimidazolyl]methylthio)pyridine

A solution of 4-chloromethyl-5-methylimidazole, hydrochloride (1.67 g) in hot ethanol (25 ml) was filtered and then added to a solution of 4-mercaptopyridine (1.1 g) in hot ethanol (25 ml) under nitrogen. The mixture was refluxed under nitrogen for 2½ hours. After cooling to room temperature, a solid was precipitated out by the addition of diethyl ether. This was removed by filtration and dried to give the title compound as the dihydrochloride, hemihydrate (1 g, 35%) mp 240°–4° C. (Found: C, 41.55; H, 4.7; N, 14.6%. $C_{10}H_{11}N_3S.2HCl.\frac{1}{2}H_2O$ requires: C, 41.8; H, 4.9; N, 14.6%).

EXAMPLE 8

2-(4-Imidazolylmethylthio)pyridine

A solution of 4-chloromethylimidazole, hydrochloride (3.8 g) in hot ethanol (25 ml) was treated with a solution of 2-mercaptopyridine (2.75 g) in hot ethanol (25 ml). The mixture was heated under reflux for 1 hour and then allowed to cool to room temperature. The resulting solid was removed by filtration and dried to give the title compound as the dihydrochloride salt (5.2 g, 79%) mp 224°–6° C. (Found: C, 41.0; H, 4.3; N, 15.9. $C_9H_9N_3S.2HCl$ requires: C, 40.9; H, 4.2; N, 15.9%).

EXAMPLE 9

1-Methyl-2-([(4-pyridyl)methyl]thio)pyridinium chloride

1-Methyl-2-pyridothione (1.25 g) was added to a solution of 4-picolyl chloride, hydrochloride (1.64 g) in hot isopropyl alcohol (20 ml). The mixture was heated under reflux for 2 hours and then allowed to cool to room temperature. The resulting solid was removed by filtration and dried to give the title compound as the hydrochloride salt, three quarter hydrate (2.5 g; 83%) mp 178°–83° C. decomp. (Found: C, 47.75; H, 5.4; N, 9.1%. $C_{12}H_{13}ClN_2S.HCl.\frac{3}{4}H_2O$ requires: C, 47.6; H, 5.2; N, 9.25%).

EXAMPLE 10

1-Methyl-2([(2-quinolyl)methyl]thio)pyridinium chloride

1-Methyl-2-pyridothione (1.25 g) was added to a solution of 2-(chloromethyl)quinoline (2.14 g) in hot acetonitrile (35 ml). The mixture was heated under reflux for 3 hours. It was then allowed to cool to room temperature and was evaporated to dryness under reduced pressure. The residue was triturated with a small amount of hot acetonitrile. The resulting solid was removed by filtration and dried to give the title compound as the hydrochloride salt, monohydrate (1.8 g; 50%) mp 142°–45° C. (Found: C, 53.9; H, 5.15; N, 8.0%. $C_{16}H_{15}ClN_2S.HCl. H_2O$ requires: C, 53.8; H, 5.1; N, 7.8%).

EXAMPLE 11

1-Methyl-2-[(2-piperidinoethyl)thio]pyridinium chloride

A solution of N-(2-chloroethyl)piperidine, hydrochloride (1.84 g) in ethanol (20 ml) was treated with 1-methyl-2-pyridothione (1.25 g) and the mixture was heated in a stainless steel bomb at 120° C. for 5 hours. It was then allowed to cool to room temperature and the solvent was removed by evaporation. The residue was triturated with ether and the resulting solid was removed by filtration and dried to give the title compound as the hydrochloride, one and one half hydrate (2.7 g; 80%) mp 188°–90° C. (Found: C, 46.7; H, 7.1; N, 8.3%. $C_{13}H_{21}ClN_2S \cdot HCl \cdot 1\frac{1}{2}H_2O$ requires: C, 46.4; H, 7.5; N, 8.3%).

EXAMPLE 12

Using the method of example 2, 2-chloromethylpyridine is reacted with the following pyridothiones to give the product indicated:

| Pyridothione | Product |
| --- | --- |
| (a) 3-hydroxymethyl-1-phenyl-2-pyridothione | 1-phenyl-3-hydroxymethyl-2-((2-pyridyl)methylthio)pyridinium chloride |
| (b) 3-hydroxy-2-pyridothione | 3-hydroxy-2-((2-pyridyl)methylthio)pyridine |
| (c) 1,4-dimethyl-2-pyridothione | 2-((2-pyridyl)methylthio)-1,4-dimethylpyridinium chloride |
| (d) 3-(2-phenylethyl)-2-pyridothione | 3-(2-phenylethyl)-2-((2-pyridyl)methylthio)pyridine |
| (e) 3-phenyl-2-pyridothione | 3-phenyl-2-((2-pyridyl)methylthio)pyridine |
| (f) 5-chloro-2-pyridothione | 5-chloro-2-((2-pyridyl)methylthio)pyridine |
| (g) 3-formyl-1-methyl-2-pyridothione | 3-formyl-1-methyl-2-(((2-pyridyl)methyl)thio)pyridinium chloride |
| (h) 3-hydroxymethyl-1-methyl-2-pyridothione | 3-hydroxymethyl-1-methyl-2-(((2-pyridyl methyl)thio)pyridinium chloride |
| (i) 3-diethoxymethyl-1-methyl-2-pyridothione | 3-diethoxymethyl-1-methyl-2-(((2-pyridyl)methyl)thio)pyridinium chloride |

EXAMPLE 13

Using the method of example 2, 1-methyl-2-pyridothione is reacted with the following starting materials to give the product indicated:

| Starting Material | Product |
| --- | --- |
| (a) 2-chloromethyl-6-methylpyridine | 2-((2-(6-methyl pyridyl)methylthio)-1-methyl-pyridinium chloride |
| (b) 2-bromomethyl-6-chloropyridine | 2-(2-(6-chloro)pyridyl)methylthio)-1-methylpyridinium bromide |
| (c) 2-chloromethyl-4-(-4-chlorophenyl pyridine | 2-((2-(4-(4-chlorophenyl))pyridyl)methylthio)-1-methylpyridinium chloride |

| Compound [Product of Example No.] | Pharmacological Test Results | | | |
| --- | --- | --- | --- | --- |
| | Sress-induced erosion (Senay & Levine) | | Anti-secretory (Shay et al) | |
| | Dose mg/kg | % inhibition | Dose mg/kg | % change in volume |
| 1 | 100 | 69 | 30 | −65 |
| | | | 10 | −43 |
| 2 | 100 | 50 | 30 | −31 |
| 3 | 100 | 67 | 30 | −71 |
| | | | 10 | −43 |
| 4 | 100 | 83 | 30 | −87 |
| | 30 | 58 | 10 | −33 |
| 5 | 100 | 58 | 30 | −55 |
| 6 | 10 | 68 | 30 | — |
| | 3 | 56 | | |
| 7 | 100 | 87 | 30 | −60 |
| 8 | 100 | 79 | 30 | — |
| | 30 | 70 | | |
| 11 | 100 | — | 30 | −35 |

ANTIHYPERTENSIVE ACTIVITY

Some compounds of the invention were tested for anti-hypertensive activity by the following procedures.

PROCEDURE A

Systolic pressure of male spontaneously hypertensive rats is measured by an indirect technique using the Decker Caudal Plethylsmograph or other appropriate sensor. Groups usually consist of 4 rats. Drugs are usually administered orally. Pressures are usually read prior to drug administration and at 1.5, 4 and 24 hours thereafter. This schedule may be altered depending upon the behaviour of the drug.

Compounds of the following examples showed activity in this test at the dose stated. 75 mg/kg orally; Examples 3 and 5. 50 mg/kg orally; Examples 9 and 10.

The compound of Example 6 was inactive in this test at 75 mg/kg.

PROCEDURE B

Female rats are rendered hypertensive by unilateral nephrectomy and the s.c. implantation of a pellet containing 30 mg of deoxycorticosterone acetate. The drinking water is replaced by normal saline ad lib for the first four weeks following preparation. Blood pressures stabilise at a hypertensive level after 6 weeks. Systolic pressure is measured indirectly before dosing with a test compound using an E and M pneumatic pulse transducer and a Devices MX2 recorder. Groups of 4 rats are dosed orally with suspensions or solutions of the test compound in 0.5% hydroxypropyl-methylcellulose 0.9% saline vehicle. Blood pressures are recorded again at 2, 6 and 24 hours and the results, expressed as a percentage of the pre-dose values compared with those of a similar group of rats receiving vehicle alone.

The compound of Example 4 was active in this test at 50 mg/kg orally. The compounds of examples 1 and 7 were inactive in this test at 50 mg/kg orally.

PHARMACEUTICAL COMPOSITIONS

The following examples illustrate the preparation of unit dosage form of pharmaceutical compositions according to the invention.

EXAMPLE A

| Antacid Tablet (chewable) | |
| --- | --- |
| Saccharin | 1.0 mg. |
| Hydrated alumina sucrose powder | 750.0 mg. |
| N—Methyl-2(4-[5-methylimidazolyl]-methylthio)pyridinium chloride | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg |

Antacid tablets of the above formulation are prepared by the following procedure. Triturate peppermint oil with talc (screen 40 mesh). Add the triturate, and other ingredients to a blender and mix thoroughly. Slug the power to large hard slugs. Granulate the slugs through a 14 mesh screen. Compress the granules on a suitable compression machine to give tablets of the required size.

EXAMPLE B

| Anti-ulcer tablet (without antacid) | mg/tablet |
|---|---|
| N—Methyl-2(4-[5-methylimidazolyl]methylthio pyridinium chloride | 100 mg. |
| Celutab | 147.5 mg. |
| Mg. Stearate | 2.5 mg. |
|  | 250.0 mg. |

The tablets are prepared by the following method. Blend the ingredients in a suitable blender. Compress the blended ingredients on a suitable compression machine to form tablets of the above composition. Celutab is a commercial product comprising 90–2% dextrose, 3–5% maltose, the remainder being higher glucose saccharides. The product is spray crystallised.

EXAMPLES C TO F

Example A is repeated but replacing N-methyl-2(4-[5-methylimidazolyl]-methylthio)pyridinium chloride with 100 mg of the products of Examples 3, 4, 5 and 7 respectively.

EXAMPLES G TO H

Example B is repeated but replacing N-methyl-2(4-[5-methylimidazolyl]-methylthio)pyridinium chloride with 100 mg of the products of Examples 3, 4, 5 and 7 respectively.

The invention includes a method for the treatment of ulcers or hypersecretion in mammals which method comprises administering to said mammal an effective amount of an anti-ulcer agent of formula I as defined above. The amount of compound used will depend on the needs of the mammal being treated and the activity of the compound. Doses may range from 1 to 100 mg/kg.

We claim:

1. A compound which is 1-methyl-2-[(piperidinoethyl)thio]pyridinium chloride.

* * * * *

UNITED STATES PATENT AND TRADEMARK OFFICE
CERTIFICATE OF CORRECTION

PATENT NO. : 4,546,187
DATED : October 8, 1985
INVENTOR(S) : Roger Crossley and Kay Helen Dickinson It is certified that error appears in the above—identified patent and that said Letters Patent are hereby corrected as shown below:

In Column 4, line 28, delete "for" and insert therefor — or —.

Signed and Sealed this

Twenty-eighth Day of January 1986

[SEAL]

Attest:

DONALD J. QUIGG

Attesting Officer      Commissioner of Patents and Trademarks